US004001696B2

United States Statutory Invention Registration [19]

[11] Reg. Number: H1696

[45] Published: Nov. 4, 1997

Adjei et al.

[54] PROCESS FOR MAKING SULFONYL ISOCYANATES

[75] Inventors: David Akueteh Adjei, Hockessin; Charles T. Blaisdell, Middletown, both of Del.

[73] Assignee: E. I. Du Pont de Nemours and Company, Wilmington, Del.

[21] Appl. No.: 793,188

[22] PCT Filed: Jul. 21, 1995

[86] PCT No.: PCT/US95/08966

§ 371 Date: Feb. 21, 1997

§ 102(e) Date: Feb. 21, 1997

[87] PCT Pub. No.: WO96/06826

PCT Pub. Date: Mar. 7, 1996

[51] Int. Cl.[6] ..... C07C 291/10

[52] U.S. Cl. ..... 560/12

*Primary Examiner*—Charles T. Jordan
*Assistant Examiner*—Meena Chelliah
*Attorney, Agent, or Firm*—Elliott A. Katz

[57] ABSTRACT

This invention relates to an improved method of making sulfonyl isocyanates from the corresponding sulfonamides and phosgene.

4 Claims, No Drawings

A statutory invention registration is not a patent. It has the defensive attributes of a patent but does not have the enforceable attributes of a patent. No article or advertisement or the like may use the term patent, or any term suggestive of a patent, when referring to a statutory invention registration. For more specific information on the rights associated with a statutory invention registration see 35 U.S.C. 157.

PROCESS FOR MAKING SULFONYL ISOCYANATES

BACKGROUND OF THE INVENTION

The present invention pertains to an improved process for making sulfonyl isocyanates from the corresponding sulfonamides and phosgene. Sulfonyl isocyanates are useful intermediates in the preparation of fine chemicals such as pesticides, including sulfonylurea herbicides, and pharmaceuticals.

U.S. Pat. No. 4,238,621 discloses the preparation of sulfonyl isocyanates from a reaction mixture of the corresponding sulfonamides and phosgene wherein the sulfonamide is generally present in molar excess in the reaction mixture relative to phosgene. In the present invention, the phosgene is always in molar excess relative to sulfonamide, thereby providing better yield and shorter reaction times.

SUMMARY OF THE INVENTION

The present invention pertains to an improved process for the preparation of sulfonyl isocyanates of Formula I comprising adding the corresponding sulfonamide of Formula II in small increments or continuously, perferably continuously, to a reaction mixture comprising inert solvent, phosgene and catalyst according to equation 1

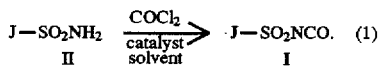

wherein J is

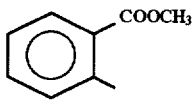

J-1

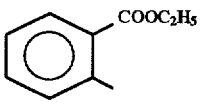

J-2

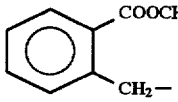

J-3

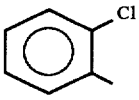

J-4

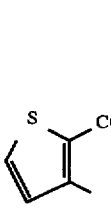

J-5

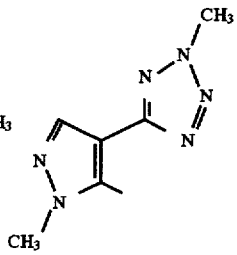

J-6

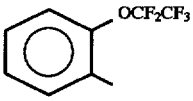

J-7

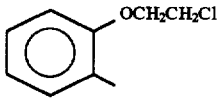

J-8 such that there is in the reaction mixture an excess of phosgene relative to sulfonamide.

The most preferred sulfonyl isocyanate is methyl 2-(isocyanatosulfonyl)benzoate.

DETAILED DESCRIPTION OF THE INVENTION

According to the present invention, sulfonamide II is fed to a reaction mixture of inert solvent, catalyst and phosgene wherein it is converted to isocyanate I. Elevated temperatures, typically in the range of 100° to 200° C., preferably 120° to 135° C., are usually required to make the reaction proceed at practical rates. Pressure can be ambient up to about 2 atmospheres (about 200 kPa). Phosgene is replenished to the reaction mixture so that at any point during the reaction there is always present a molar excess of phosgene (hereinafter referred to as "phosgene-rich") relative to sulfonamide; preferably there is at least 2% by weight of phosgene in the reaction mixture, more preferably at least 5%. Sulfonamide can be fed to the reaction mixture in small increments or continuously, preferably continuously, and can be in the form of a slurry or solution in solvent, preferably as concentrated as possible. The slurry can be preheated before admission to the reactor.

Solvent can be any inert solvent with a boiling point at or above the desired reaction temperature; examples include xylene, chlorobenzene, mesitylene, toluene, pentachloroethane and octane.

Catalysts include (U.S. Pat. No. 4,238,621) carbaryl isocyanates such as butyl isocyanate and tertiary amines such as 1,4-diaza[2,2,2]bicyclooctane (DABCO). The full charge of catalyst can be added to the initial reaction mixture, or added incrementally or continuously during the course of reaction. Feeding the catalyst over the course of the reaction can reduce the total amount of catalyst needed and reduce side reactions.

Catalysts also include sulfonyl isocyanates (Res. Discl. (1983) 23210, 261), preferably the product sulfonyl isofonyl isocyanate. The sulfonyl isocyanate need not be isolated, and a small portion of the product reaction mixture (referred to as a "heel") from a previous batch can be employed as catalyst in a subsequent batch.

The reaction of sulfonamide and phosgene is very rapid and exothermic, and HCl is generated as a byproduct. It is preferable to drive the HCl out of the reaction mixture as rapidly as possible, preferably by maintaining vigorous reflux of phosgene, so that side-reactions caused by the HCl, and the resulting yield losses, are minimized. The HCl off-gas will typically be captured by scrubbers so as to avoid release to the environment; the phosgene can be condensed and returned to the reaction mixture. The HCl generation can be used to monitor the course of the reaction and can also be used to maintain an appropriate sulfonamide feed rate and concentration so that the reaction is kept under control and reaction times are as short as possible.

Once the reaction is complete, excess phosgene and dissolved HCl can be removed from the mixture by standard methods such as distillation. The sulfonyl isocyanate can be recovered by standard methods, such as crystallization and filtration. Alternatively, the sulfonyl isocyanate can be reacted further, with or without isolation, to form, for example, a sulfonylurea herbicide as described in U.S. Pat. No. 4,238,621, column 5, lines 14–20.

In accordance with this invention, improved yields of sulfonyl isocyanate are obtained with less reaction time. The critical feature of the present invention is the reaction of sulfonamide in a phosgene-rich environment throughout substantially the entire process. In contrast, known methods for producing sulfonyl isocyanate from sulfonamide add phosgene to a reaction mixture of sulfonamide such that throughout substantially the entire reaction the sulfonamide is in excess relative to phosgene.

EXAMPLES

The examples which follow demonstrate the improved process of the present invention. Comparative Example A is provided as an illustration of the state of the art as disclosed in U.S. Pat. No. 4,238,621 and Res. Discl. (1983) 23210, 261. The same reactor was employed throughout. In all examples the sulfonyl isocyanate is methyl 2-(isocyanatosulfonyl)benzoate and the sulfonamide is methyl 2-(aminosulfonyl)-benzoate.

The reactor is a Pfaudler 7500 L reactor which was jacketed for steam heating and which was equipped with a reflux condenser capable of cooling to −30° C. to recover refluxing phosgene. The reactor has an inlet port for admitting reactants, an exit port for recovering product and an agitator for thorough mixing of ingredients during reaction.

Summary of Ingredients and Parameters

| | Example 1 | Example 2 | Example 3 | Example A |
|---|---|---|---|---|
| Sulfonamide (kG) | 771.8 | 1452.8 | 1589 | 771.8 |
| Butyl isocyanate (kG) | 32 | 72.6 | 72.6 | 71.7 |
| Xylene (kG) | 2679 | 2679 | 2679 | 2679 |
| *Heel (kG) | 898.9 | 911.6 | 961.6 | 972.5 |
| Reaction Temperature (°C.) | 126–130 | 126–130 | 126–130 | 126–130 |
| Reaction time (hours) | 2.5 | 7.2 | 7.5 | 3.4 |
| % yield sulfonyl isocyanate (based on sulfonamide) | 95.1 | 94.4 | 95.1 | 87.7 |

*Heel is comprised of sulfonyl isocyanate and solvent, and is the product reaction mixture from a previous batch.

Example 1

A heel from a previous batch was present in the reactor. A slurry of xylene and sulfonamide was made in a separate vessel. The reactor was heated to about 130° C. after which phosgene was added until the reactor mixture was saturated with same (about 3% by weight of the reaction mass) at 127° C. While maintaining vigorous reflux conditions, continuous feed of sulfonamide slurry and butyl isocyanate was started simultaneously. The slurry feed rate was 2 kG/min; the butyl isocyanate rate was about a 10% molar ratio relative to sufonamide and was maintained throughout the entire course of slurry addition. The operating pressure was monitored as an indication of HCl off-gas generation. During the course of the reaction, phosgene was replenished to the reactor as needed to maintain reaction temperature and so that the reaction mixture was always saturated with same. When the reaction was complete, the residual HCl and phosgene was stripped from the reaction mixture by solvent distillation and by sparging with nitrogen under reflux and as the reaction mixture cooled. The reaction mixture was analyzed for sulfonyl isocyanate and the yield calculated.

Example 2

Example 2 was run as described in Example 1 except using the quantities and conditions noted in the summary above.

Example 3

Example 3 was run as described in Example 1 except using the quantities and conditions noted in the summary above.

Comparative Example A

A heel from a previous batch was present in the reactor. The sulfonamide was slurried with xylene in a separate vessel and then the entire charge was transferred to the reactor containing the heel. The butyl isocyanate was then added to the reactor after which the reactor was brought up to reaction temperature. The continuous phosgene feed was then started at a rate of about 150 kG/hr, and adjusted as necessary to maintain a steady operating pressure as HCl is generated. When the reaction was complete, as indicated by the cessation of phosgene consumption, the residual HCl and phosgene was stripped from the reaction mixture by solvent distillation and by sparging with nitrogen under reflux and as the reaction mixture cooled. The reaction mixture was analyzed for sulfonyl isocyanate and the yield calculated.

We claim:

1. In a process for making a compound of the formula $$J—SO_2NCO$$

wherein

J is

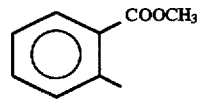

J-1

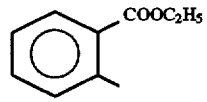

J-2

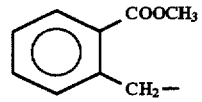

J-3

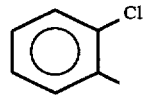

J-4

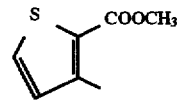

J-5

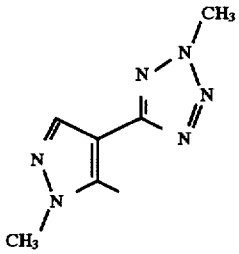

J-6

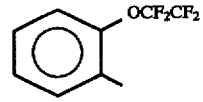

J-7

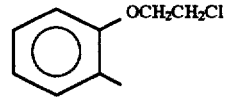

J-8 by reacting a compound of the formula $J—SO_2NH_2$ with phosgene in a reaction mixture comprising the compound $J—SO_2NH_2$, phosgene and a solvent, the improvement comprising conducting the reaction in the presence of a molar excess of phosgene relative to the compound $J—SO_2NH_2$.

2. The process of claim 1 wherein the percent by weight of phosgene in the reaction mixture is at least 2%.

3. The process of claim 2 wherein the percent by weight of phosgene in the reaction mixture is at least 5%.

4. The process of claim 1 wherein J is J–1.

* * * * *